US012784881B2

(12) United States Patent
Nash et al.

(10) Patent No.: US 12,784,881 B2
(45) Date of Patent: Nov. 3, 2026

(54) AUTOMATED NOTIFICATIONS OF CHANGES TO MEDICAL RECORDS

(71) Applicant: MatrixCare, Inc., Bloomington, MN (US)

(72) Inventors: Frank Nash, Bloomington, MN (US); Adhiraj Ganpat Prajapati, Bloomington, MN (US); Mary Camp, Bloomington, MN (US)

(73) Assignee: MatrixCare, Inc., Bloomington, MN (US)

(*) Notice: Subject to any disclaimer, the term of this patent is extended or adjusted under 35 U.S.C. 154(b) by 541 days.

(21) Appl. No.: 17/644,729

(22) Filed: Dec. 16, 2021

(65) Prior Publication Data

US 2023/0197217 A1 Jun. 22, 2023

(51) Int. Cl.

*G16H 10/60* (2018.01)
*G06F 9/451* (2018.01)
*G16H 80/00* (2018.01)
*H04L 9/40* (2022.01)

(52) U.S. Cl.

CPC ............. *G16H 10/60* (2018.01); *G06F 9/451* (2018.02); *G16H 80/00* (2018.01); *H04L 63/10* (2013.01)

(58) Field of Classification Search

CPC .......... G16H 10/60; G06F 9/451; H04L 63/10
See application file for complete search history.

(56) References Cited

U.S. PATENT DOCUMENTS

| | | | | |
|---|---|---|---|---|
| 2006/0149416 | A1* | 7/2006 | Mohapatra | G16H 20/10 700/242 |
| 2013/0060580 | A1* | 3/2013 | Chapman | G16H 20/70 705/2 |
| 2013/0159021 | A1* | 6/2013 | Felsher | G16H 10/60 705/3 |
| 2018/0294052 | A1* | 10/2018 | Fishman | G06Q 10/1093 |
| 2020/0060603 | A1* | 2/2020 | Bower | A61B 5/4082 |
| 2021/0319872 | A1* | 10/2021 | Valentine | G16H 40/67 |

* cited by examiner

*Primary Examiner* — Reginald R Reyes
(74) *Attorney, Agent, or Firm* — Patterson + Sheridan, LLP

(57) ABSTRACT

Embodiments herein describe an automated notification system that can detect a change to a person's medical record, notify an authorized person (e.g., a family member), and direct the authorized person to a health portal to view the change. The health portal then authenticates the person to ensure they are authorized to access the health record. Once authenticated, the health portal displays a graphical user interface (GUI) that includes both the older information in the medical record as well as the change in the record (e.g., a new diagnosis or new medication). The GUI can use a visual indicator to emphasize the change to the medical record to easily distinguish it from the older information (e.g., previous diagnosis and medications).

19 Claims, 8 Drawing Sheets

AUTOMATED NOTIFICATIONS OF CHANGES TO MEDICAL RECORDS

BACKGROUND

Field

Aspects of the present disclosure relate to an automated system for providing notifications or alerts regarding changes to a medical record.

Description of the Related Art

Many patient care facilities (e.g., hospitals, clinics, rehabilitation centers, long term care centers, etc.) offer, or are required, to alert an authorized person when there is a change to a patient's medical record. This requires an employee to call the authorized person and inform them of the change in the record. As such, providing notifications can require an employee to identify there has been a change and then call the authorized person (or persons) to explain the change to them. This requires a substantial amount of employee time to properly manage these notifications. Further, the employee may be unable to authenticate the person over the phone. Thus, they may not be sure the person they are talking to is the authorized person.

SUMMARY

Certain embodiments provide a method that includes receiving an update to a medical record, determining, using a rule set, that an authorized person should be notified of the update, generating a notification for the authorized person corresponding to the update, initiating a transmission of an electronic communication to the authorized person that comprises the notification, authenticating the authorized person at a health portal, and after authenticating the authorized person, generating a graphical user interface (GUI) including a visual indicator to emphasize the update to the medical record relative to older information in the medical record also displayed in the GUI.

Other embodiments provide a non-transitory computer readable medium comprising instructions to be executed in a processor, the instructions when executed in the processor perform an operation. The operation includes receiving an update to a medical record, determining, using a rule set, that an authorized person should be notified of the update, generating a notification for the authorized person corresponding to the update, initiating a transmission of an electronic communication to the authorized person that comprises the notification, authenticating the authorized person at a health portal, and after authenticating the authorized person, generating a GUI including a visual indicator to emphasize the update to the medical record relative to older information in the medical record also displayed in the GUI.

Other embodiments provide a system that includes a processor and memory comprising instructions that, when executed by the processor, perform an operation. The operation includes receiving an update to a medical record, determining, using a rule set, that an authorized person should be notified of the update, generating a notification for the authorized person corresponding to the update, initiating a transmission of an electronic communication to the authorized person that comprises the notification, authenticating the authorized person at a health portal, and after authenticating the authorized person, generating a GUI including a visual indicator to emphasize the update to the medical record relative to older information in the medical record also displayed in the GUI.

The following description and the related drawings set forth in detail certain illustrative features of one or more embodiments.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
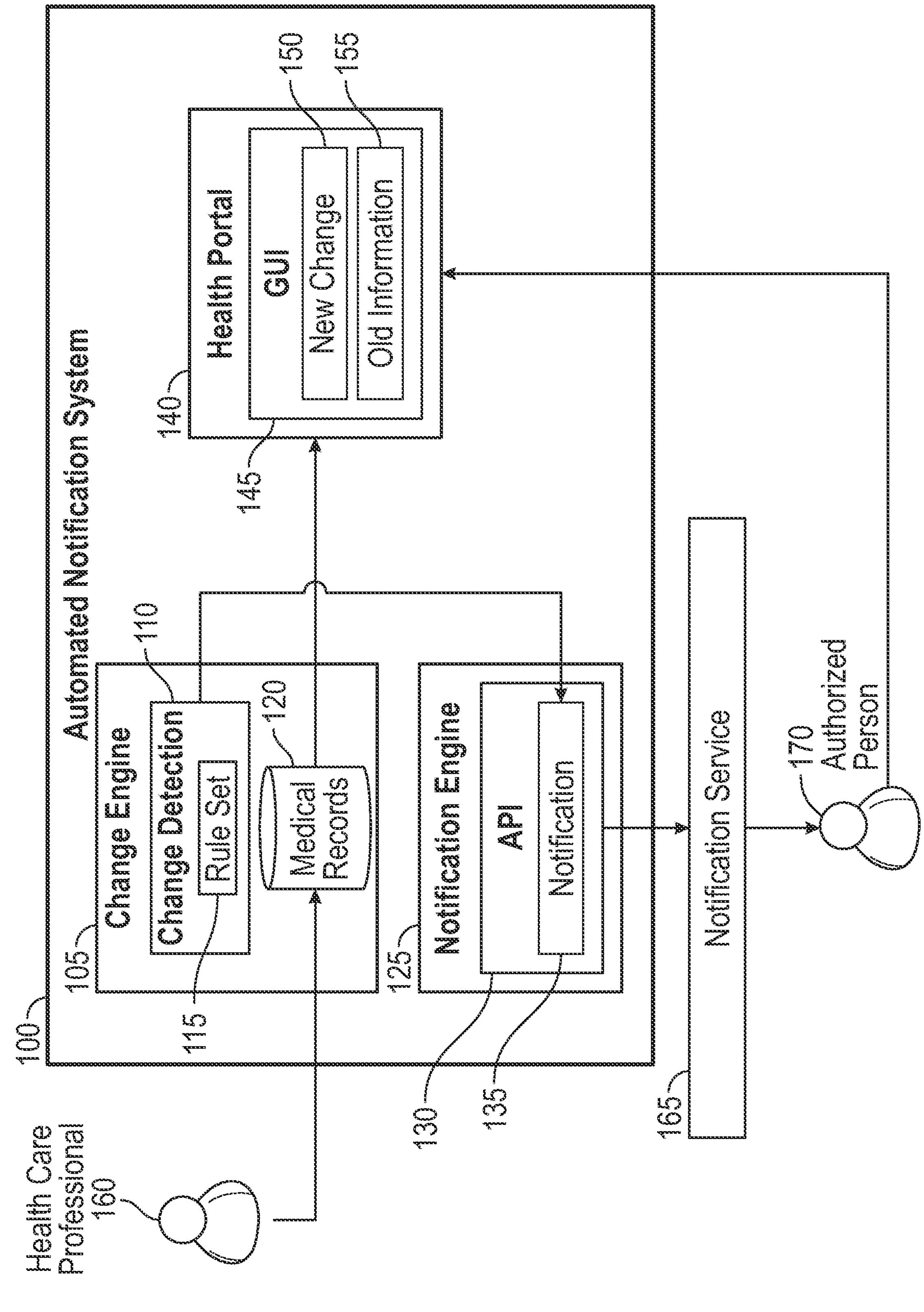
FIG. 1 illustrates an automated notification system for providing an authorized person with updated information regarding changes to a medical history, according to one embodiment.

Embodiments herein describe an automated notification system that can detect a change to a person's medical record, notify an authorized person (e.g., a family member), and direct the authorized person to a health portal to view the change. The health portal then authenticates the person to ensure they are authorized to access the health record. Once authenticated, the health portal displays a graphical user interface (GUI) that includes both the older information in the medical record as well as the change in the record (e.g., a new diagnosis or new medication). The GUI can use a visual indicator to emphasize the change to the medical record to easily distinguish it from the older information (e.g., previous diagnoses and medications). For example, the new information can be highlighted, bolded, or separated from the old information in the medical record. In this manner, the automated notification system can leverage a computing environment to transmit an electronic notification, authenticate the person before they are permitted to access the health portal, and then, once authenticated, display a GUI containing the updated information all without any intervention by an employee of a healthcare provider. That is, the current embodiments use computer technology to authenticate a person (e.g., using security credentials or biometric information) and then provide the updated information using a secure health portal and a GUI, all of which could not be used in the previous technique where an employee calls the authorized person and simply conveys the change in the medical record orally.

In addition, the GUI can include educational information for the new, updated information. For example, if the medical record includes a new diagnosis of an illness, the GUI can include educational information providing a description of the illness and known symptoms and treatments. If the medical record includes a new medication, the GUI can include educational information such as side effects, dosage recommendations, and the length of time patients are typically on the medication, and the like. Further, this educational information can be pulled from a vetted information source such as a government entity or the drug manufacturer.

Using the embodiments herein, the GUI can first emphasize new or changed medical data based on tracking changes to the electronic medical record and then automatically rearrange the displayed medical data so it appears near the top of the GUI and add visual indicators relative to the old information displayed in the GUI the previous time the person logged into the health portal. In addition, the GUI can automatically pull educational information from third-party sources and insert this information at relevant parts in the GUI. Additionally and alternatively, the GUI can embed a link to the third-party source that launches a web browser to take the authorized person to the source. This can improve the user interface by querying and pulling information from trusted third-party sources related to the changed medical information and embedding this information into the GUI, or by providing links to trusted third-party sources that are selectable by the authorized person to launch applications (e.g., a web browser) to access those sources.

FIG. 1 illustrates an automated notification system 100 for providing an authorized person 170 with updated information regarding changes to a medical history, according to one embodiment. As shown, the automated notification system 100 includes a change engine 105 which receives updates (or changes) to medical records 120 from a healthcare professional 160. The healthcare professional 160 could be a nurse, physician, physician's assistant, healthcare administrator, and the like. In one embodiment, the update to the medical records 120 may include a new diagnosis of an illness or medical condition or a new medication for a patient. Or the update can be the removal of a diagnosis (e.g., the patient has recovered) or the removal of a medication. However, in some embodiments, the automated notification system 100 may transmit a notification only for the new updates, but not when removing a diagnosis or medication.

In one embodiment, the medical records 120 are the records of patients currently in patient care facilities (e.g., hospitals, clinics, rehabilitation centers, long term care centers, etc.) but this is not a requirement. The automated notification system 100 can be used to send notifications regarding changes of medical records 120 for persons who are not currently admitted in a facility.

In addition to storing (or having access to) the medical records 120, the change engine 105 includes a change detector 110 for determining when to send a notification to the authorized person 170. In this example, the change detector 110 includes a rule set 115 that defines in which situations the authorized person 170 should be notified and in which situations the person 170 does not need to be notified. In one example, the rule set 115 may indicate that all changes to a medical record 120 for a first person should be reported to an authorized person 170, while only some changes for the medical record 120 for a second person should be reported to an authorized person. In another example, the rule set 115 may indicate that the addition or removal of diagnoses or medications should be reported to the authorized person while other changes to the medical records 120, such as changes to assigned nurses/physicians, changes in a diet, changes to diagnostic information (e.g., blood pressure or glucose levels), are not. In yet another example, the rule set 115 may further distinguish between different types of diagnoses or medications. If the physician adds an over-the-counter medication to the medical record 120, this may not trigger a notification to the authorized person 170, while the addition of a medication requiring a prescription does trigger a notification. Similarly, only certain new diagnoses would trigger a notification while others would not. In this manner, the change engine 105 can use the rule set 115 to provide customized notifications on behalf of each patient, and control which types of changes trigger an automatic notification and which do not.

The system 100 also includes a notification engine 125 that, in response to the change detector 110 identifying a change to the medical records 120 that should be reported, prepares a notification 135 for the change. In one embodiment, the information in the notification 135 may change depending on what medium is used to transmit the notification 135 to the authorized person 170. For example, if a text message (e.g., a short message service (SMS) or multimedia messaging service (MMS)) is used, the notification 135 may include the phone number of the authorized person 170, a message body, and a link the person 170 can use to access a health portal 140 to view the updated information in the medical records 120. If an email is used, the notification 135 can include the email address of the authorized person 170, a message body, and the link to the health portal 140. If a robocall is used, the notification may include an audio file (generated using, e.g., a text-to-speech software application) that includes an audio message and instructions for accessing the health portal 140.

In one embodiment, the notification includes non-protected health information that provides the authorized person 170 with a general description of the change to the medical record 120 without divulging protected health information. For example, the message body in the notification 135 may state the name of the person or patient and indicate there has a been a change to her medication without stating whether the medication was being added or removed, or without stating the specific name of the medication. This information may be protected health information that is displayed to the authorized person 170 only after they have been authenticated by the health portal 140. Thus, the health portal 140 can be referred to as a secure application or secure web portal.

The notification engine 125 includes an application programming interface (API) 130 for transmitting the notification 135 to a notification service 165. In one embodiment, the notification service 165 may be a third-party service with a contractual relationship with the entity that operates the automated notification system 100. The API 130 calls the notification service 165 and provides it with the information in the notification 135 (e.g., phone number, email address, message body, link to the health portal 140, etc.). The notification service 165 then uses this information to transmit an electronic communication to the authorizer person 170 such as an email, text message, robocall, etc. While the notification service 165 is shown as being separate from the system 100, in one embodiment, the service 165 may be a software module or application within the automated notification system 100.

The authorized person 170 can be any person who has previously been authorized to receive and view updates regarding the medical record 120 for a particular patient. In one embodiment, the medical record 120 for each patient may include a list of the authorized persons who should receive the notifications 135. Thus, each medical record 120 can list a different authorized person 170. The authorized person 170 can include a legal guardian, family member, a person with power of attorney for the patient, another physician, and the like. The authorized person 170 may be governed by law, or by consent from the patient. For example, when being admitted into a health care facility, the patient may inform the facility who are the authorized persons 170 that should be notified when her medical record 120 is updated. Further, the patient can indicate under which conditions the authorized person 170 should be notified which can be used to generate a customized rule set 115 for the patient's medical record 120 for generating the notifications 135.

The authorized person 170 can use the information received from the notification service 165 to access the health portal 140 to view the change to the medical record 120. For example, if the service 165 sends an email or text message to the authorized person 170, these electronic communications can include an embedded link that the person 170 can click or press which then opens up a web browser or launches a health provider's application (app) to direct the person 170 to access the secure health portal 140. Alternatively, the authorized person 170 may manually type in a URL for the health portal 140 into a web browser or launch the health provider's application.

The health portal 140 generates a GUI 145 which displays information retrieved from the medical records 120. In one embodiment, the health portal 140 authenticates the person 170 before they are permitted to view information contained in one of the medical records 120. For example, when clicking on or pressing a link in the notification 135, the link may direct a web browser on a user device to a login page for the health portal 140. The authorized person 170 may then have to enter security credentials to access the health portal 140. In another embodiment, if the health portal 140 is part of a health provider's app executing on the authorized person's smartphone or tablet computer, the person 170 may already be logged in and preauthorized to access the health portal 140.

In any case, the embodiments herein leverage computer technology to authenticate the authorized person 170, when previously, no such authentication was performed. This not only automates the process of conveying changes to the medical records 120, but also improves data security by ensuring the person 170 attempting to access the medical record 120 via the health portal 140 possesses the proper security credentials, which can include a username/password or biometric data. Or the app may nonetheless require the user to provide the proper security credentials (e.g., biometric ID) before they can view the information, even if the user provided those security credentials when first opening the app.

After ensuring the person logging into the health portal 140 is the authorized person 170, the health portal 140 can retrieve information from the medical record (120) (or records) the person 170 is authorized to access and generate a GUI 145 for displaying this information. The change engine 105 or the health portal 140 can track the changes in the electronic medical records 120 to identify what information is new or has been changed since the last time the authorized person 170 logged into the health portal 140. The health portal 140 can then automatically rearrange the displayed medical data so the new information appears near the top of the GUI and add visual indicators. Put differently, the change engine 105 and the health portal 140 can track the changes in the medical records 120 as well as the times the authorized person 170 has logged into the health portal 140. With this information, the change engine 105 or the health portal 140 can identify the new or updated information in the medical record 120 since the last time the person 170 logged into the health portal 140. For example, the medications and conditions on the GUI 145 can be sorted in reverse chronological order, with the newest change at the top of the GUI 145.

The health portal 140 can generate the GUI 145 to emphasize a new change 150 in the medical record 120 relative to old information 155 in the medical record 120 that has previously been seen by the authorized person 170. That is, based on tracking changes to the medical records 120 and tracking when the authorized person 170 logs into the health portal 140, the health portal 140 can identify information in the medical record 120 that has been seen previously by the person 170 (i.e., the old information 155) and new or updated information that has not been seen by the person (i.e., the new change 150). The GUI 145 can then emphasis the new change 150 relative to the old information 155. For example, the new change may be displayed above the old information 155 at the top of the GUI 145. Or there may be a line or border to divide the new change 150 from the older information 155. In some embodiments, the GUI 145 includes a visual indicator (e.g., highlighting, bold font, a different font, italics, etc.) for the new change 150, but not for the old information 155. Thus, the emphasis provided to the new change 150 can be derived from tracking the medical records 120 and the logins of the authorized person 170.

In one embodiment, rather than emphasizing all the changes made to the medical record 120 since the last time the authorized person 170 logged into the health portal 140, the GUI 145 may emphasize only the changes to the medical record 120 that triggered the notification 135. For example, there may be other changes made to the medical record 120 since the last time the authorized person 170 logged into the medical record 120, but these changes may not have triggered the notification 135 (e.g., these changes did not satisfy a rule in the rule set 115). These non-triggering changes may be grouped as the old information 155 while only the triggering changes to the medical record 120 are part of the new change 150 which is then emphasized in the GUI 145. Thus, the automated notification system 100 is configurable to track and emphasize all the changes to the medical record 120 in the GUI 145 that occurred between user logins to the health portal 140, or to emphasis in the GUI 145 only a subportion of the changes to the medical record 120 since the last login by the authorized person 170 (e.g., only the change that triggered the notification 135).

In one embodiment, the automatic notification system 100—i.e., the change engine 105, the notification engine 125 and the health portal 140—execute on separate computing systems (e.g., a separate web server, data centers, or cloud computing environments). These computing systems can then be interconnected using a private or public network. However, in another embodiment, the change engine 105, the notification engine 125 and the health portal 140 may be executed on the same computing system (e.g., the same cloud computing environment).

Figure 2:
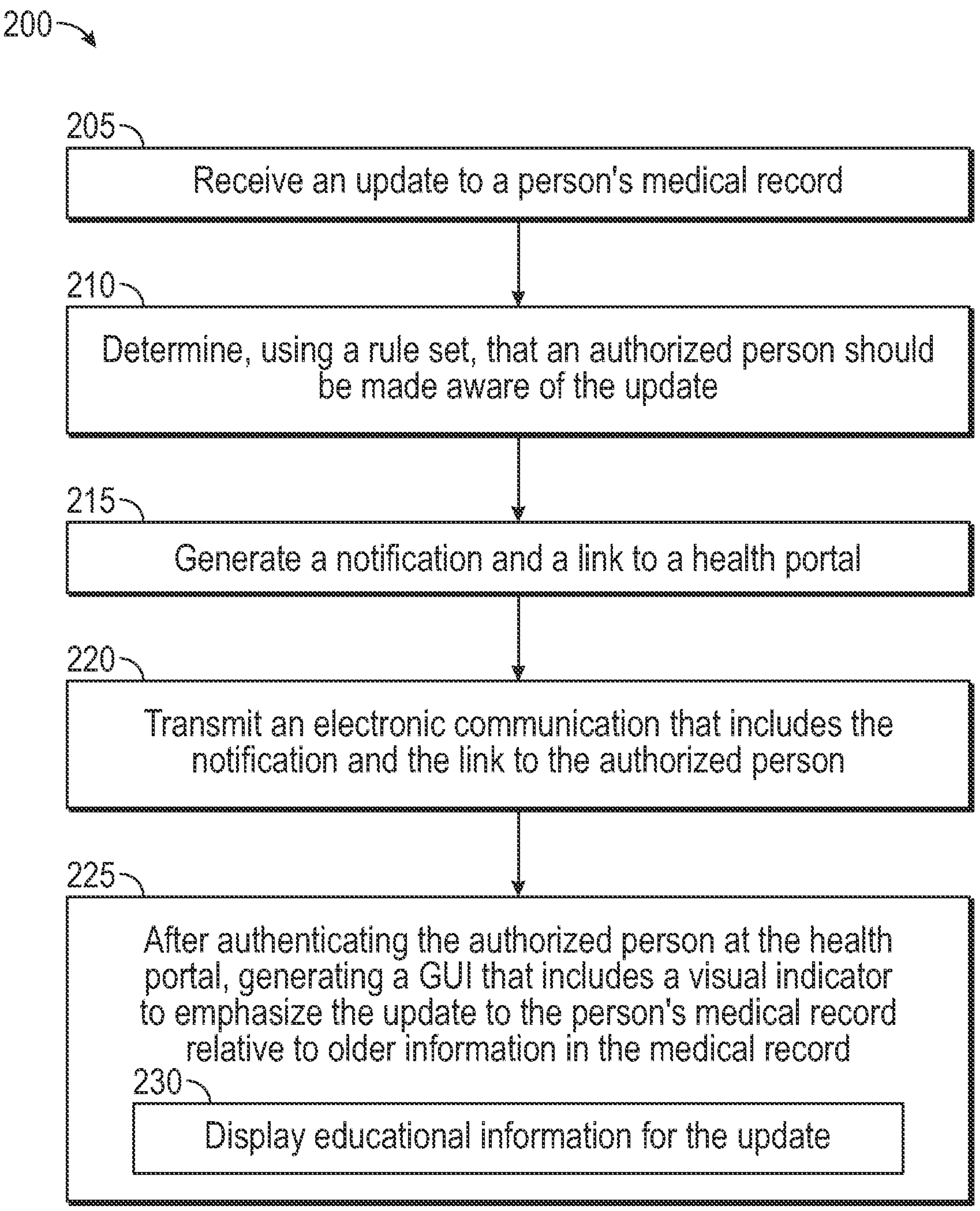
FIG. 2 is a flowchart for providing an automatic notification of a change to a medical history, according to one embodiment.

FIG. 2 is a flowchart of a method 200 for providing an automatic notification of a change to a medical history, according to one embodiment. At block 205, an automated notification system receives an update to a person's medical record. Referring to FIG. 1, the automated notification system 100 includes a change engine 105 that receives changes to medical records 120 from the healthcare professional 160. The person may be a patient admitted into a healthcare facility, but could also be someone who is being treated by the healthcare professional but has not been admitted into a facility.

The update can be provided by any electronic means. For example, the healthcare professional may use a user interface to input the change into the person's medical record. In another example, the healthcare professional may use a separate application that includes an API for interfacing with the change engine in the automated notification system.

At block 210, the change engine determines, using a rule set (e.g., the rule set 115 in FIG. 1), that an authorized person should be made aware of the update to the medical record. This authorized person is generally someone different from the person associated with the medical record. In one embodiment, the authorized person can include a legal guardian, a person with power of attorney for the patient, another healthcare professional (e.g., the person's family doctor), and the like. The authorized person may be governed by law that stipulates who should receive updates for the person associated with the medical record. In another example, the authorized person may be selected or chosen by the person when they are admitted into the healthcare facility or when they first become a patient of a physician. Further, the person may select multiple authorized persons to receive automatic notifications when there are changes to her medical record.

The rule set can be any number of rules for determining when to update the authorized person in response to an update to the person's medical record. In one embodiment, the rule set may indicate that any update to the person's medical record should be reported to the authorized person. Alternatively, the rule set may indicate that only certain types of changes should be reported to the authorized person, such as changes to diagnoses or medications but not changes in a primary care physician, changes to the person's meal plans, or changes to a person's diagnostic information such as blood pressure, heart rate, blood glucose levels, etc. In the case where the rule set indicates the update does not warrant notifying the authorized person, the automated notification system updates the medical record without transmitting any automated notification or electronic communication to the authorized person.

In another example, the rule set can stipulate that changes that add new diagnoses or new medications to the medical record should be reported to the authorized person while changes that remove diagnoses (e.g., the patient has recovered from the illness) or remove medications should not be reported. Additionally or alternatively, the rule set can establish a seriousness threshold whether changes to the medical record that are below this threshold are not reported but ones that are above this threshold are. For example, adding or removing over-the-counter medications from the medical record may be below the threshold while adding or removing prescription medications from the medical record are above the threshold. In another example, changes in diagnostic information, such as blood pressure, that are below the threshold (e.g., within a normal range) may not be reported to the authorized person while changes to diagnostic information that exceed the threshold are reported.

In one embodiment, the rule set can be customized for each person or patient. That is, each person's medical record can correspond to a different rule set used to determine when to notify an authorized person of a change. For example, a medical record for a child may have a different rule set than a medical record for an adult. For example, the parent of the child may be notified of all changes to the child's medical record while a friend or family member of an adult patient may be notified of only major changes to the adult's medical record (e.g., new diagnoses and new medications but not any other changes). In addition, the rule set can be customized by the patient or her physician. That is, the patient can add additional rules to the rule set, or subtract rules from a default, or initial, rule set.

Assuming at least one rule in the rule set is satisfied, the method 200 proceeds to block 215 where the notification engine in the automated notification system generates a notification and a link to the health portal. Referring to FIG. 1, when a rule in the rule set 115 is satisfied, the change detector 110 instructs the notification engine 125 to generate a notification 135. This notification 135 can include information used by the notification service 165 to transmit an electronic communication (e.g., a text message, email, robocall, etc.) to the authorized person 170. When the notification 135 is sent via text or email, the notification engine 125 can generate the link to the health portal. This link can be a selectable link. For example, the notification 135 can include a message that says "To access the health portal to view the change, press HERE" where the text "HERE" is a selectable link that launches a separate application to direct the user to the health portal. In another embodiment, the selectable link may be a uniform resource location (URL) or a short URL.

In one embodiment, the link launches a web browser on the person's user device which then directs the person to a website corresponding to the health portal. In another embodiment, the link launches a healthcare provider's app that may have been previously installed on the device. If the person has not yet installed the app, the link may direct the person to a website or an application store where the user can download and install the healthcare provider's app.

At block 220, the notification service transmits an electronic communication that includes the notification and the link to the authorized person. If a third-party notification service is used to transmit the electronic notification to the authorized person, the notification engine can use an API to provide to the notification service the person's contact information (phone number or email address), a message body explaining the purpose of the notification, the link (if applicable), or directions for accessing the health portal.

However, in other embodiments, the notification engine is capable of transmitting the electronic communication to the authorized person. In that case, the notification engine can send the electronic communication to the authorized person using, e.g., a public network (e.g., the Internet) or a cellular network. In any case, once the authorized person receives the electronic communication, she can read the text (or listen to the audio message) and interact with an embedded link, or follow the provided instructions, to log into the health portal.

At block 225, after authenticating the authorized person at the health portal, the health portal generates a GUI that includes a visual indicator to emphasize the update to the person's health record relative to older information in the health record.

Advantageously, the method 200 can use a secure health portal to authenticate the person—i.e., ensure that the person who is attempting to log into the health portal is the authorized person. Previously, when an employee of the healthcare provider called the authorized person, there was no practical way to ensure the person who answered the phone was the authorized person. Either the employee simply provided the change to the medical record to the person on the phone (without authenticated the person) or would have to perform a cumbersome authentication process (e.g., asking for a predefined PIN). However, the person would have to have the PIN available (or memorize it), but this is a cumbersome and unreliable. The person may have forgot the PIN or be away from the location she stored the PIN. Also, this PIN, which itself could be personal information, would have to be exposed to the healthcare employee for verification.

In contrast, by automating this process as described in method 200, an authentication step can be easily added to the process to ensure that the person who received the electronic communication is actually the authorized person. Further, the authentication can be performed electronically either using credentials entered into a website (where those credentials could be saved in a secure location in the user device) or via a native app (e.g., the healthcare provider's app). Thus, the automated process in method 200 can add an extremely secure, and practical, authentication step that ensures the person attempting to access the portal is the authorized person.

Once authenticated, the health portal generates the GUI and emphasizes the information that was updated in the person's medical record. In one embodiment, the GUI may emphasize only the updated information that triggered the notification (i.e., the change that satisfied a rule in the rule set at block 210). For example, the healthcare professional may have updated several different aspects in the medical record but only one of those updates satisfied a rule in the rule set. The health portal may emphasize only that change in the GUI while the other changes to the medical record may also be displayed in the GUI but are de-emphasized. For example, the change that satisfied the rule set may be highlighted, or moved to the top of the GUI, while the other changes (and any old information in the medical record) are not highlighted, or are listed below the triggering change.

Alternatively, the GUI may emphasize all the changes that occurred since the last time the authorized person logged into the health portal. Continuing the example above, even though some of the changes to the medical record did not satisfy the rule set, the health portal may nonetheless emphasis those changes in the GUI along with the change that did satisfy the rule set. Any old information in the medical record, which was already viewed by the authorized person, would be deemphasized. In another example, the health portal may determine the last time the authorized person logged into the health portal and identify all the changes made to the person's health record after that time. The health portal can then emphasize each of the changes in the GUI, while deemphasizing information that was already in the medical record the last time the authorized person logged into the health portal.

Figure 3A:
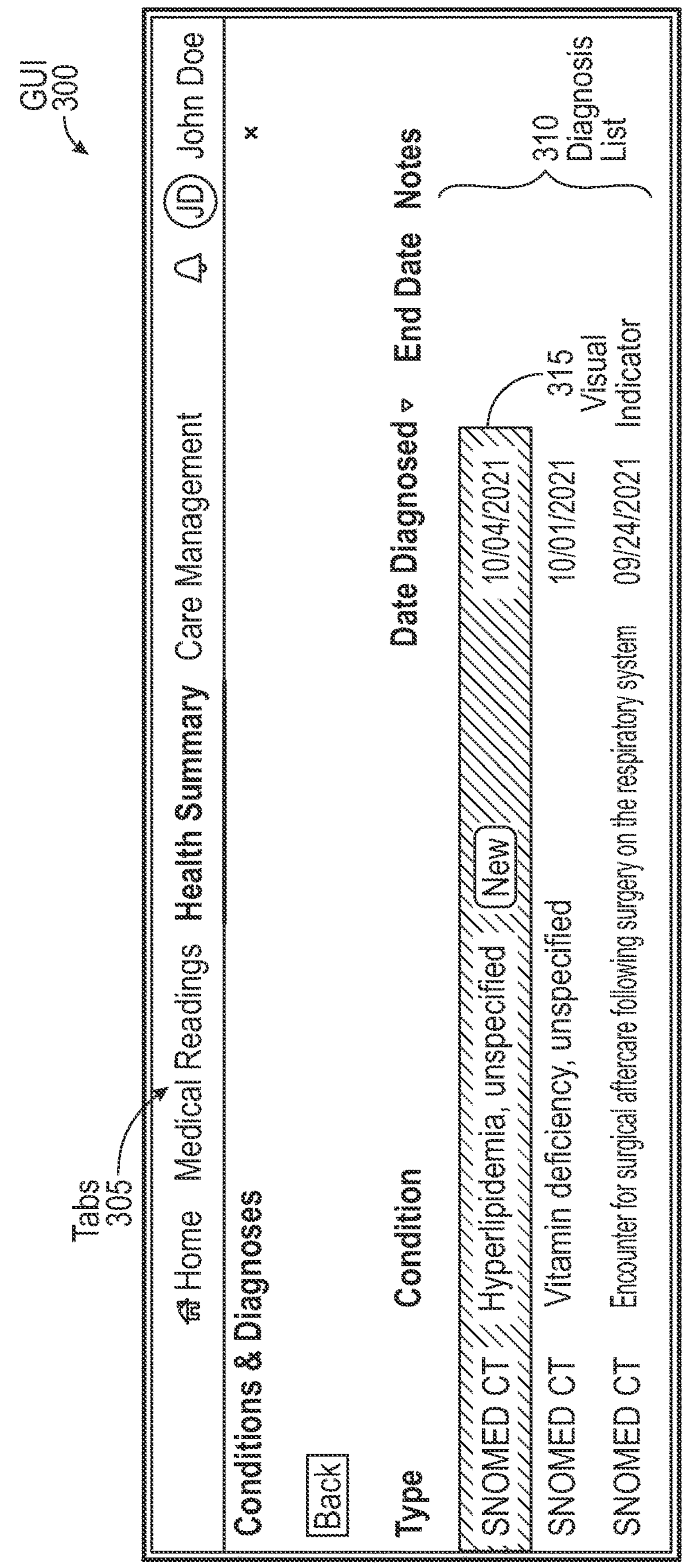
FIGS. 3A and 3B illustrate GUIs for emphasizing new information in a medical record using visual indicators, according to one embodiment.
Figure 3B:
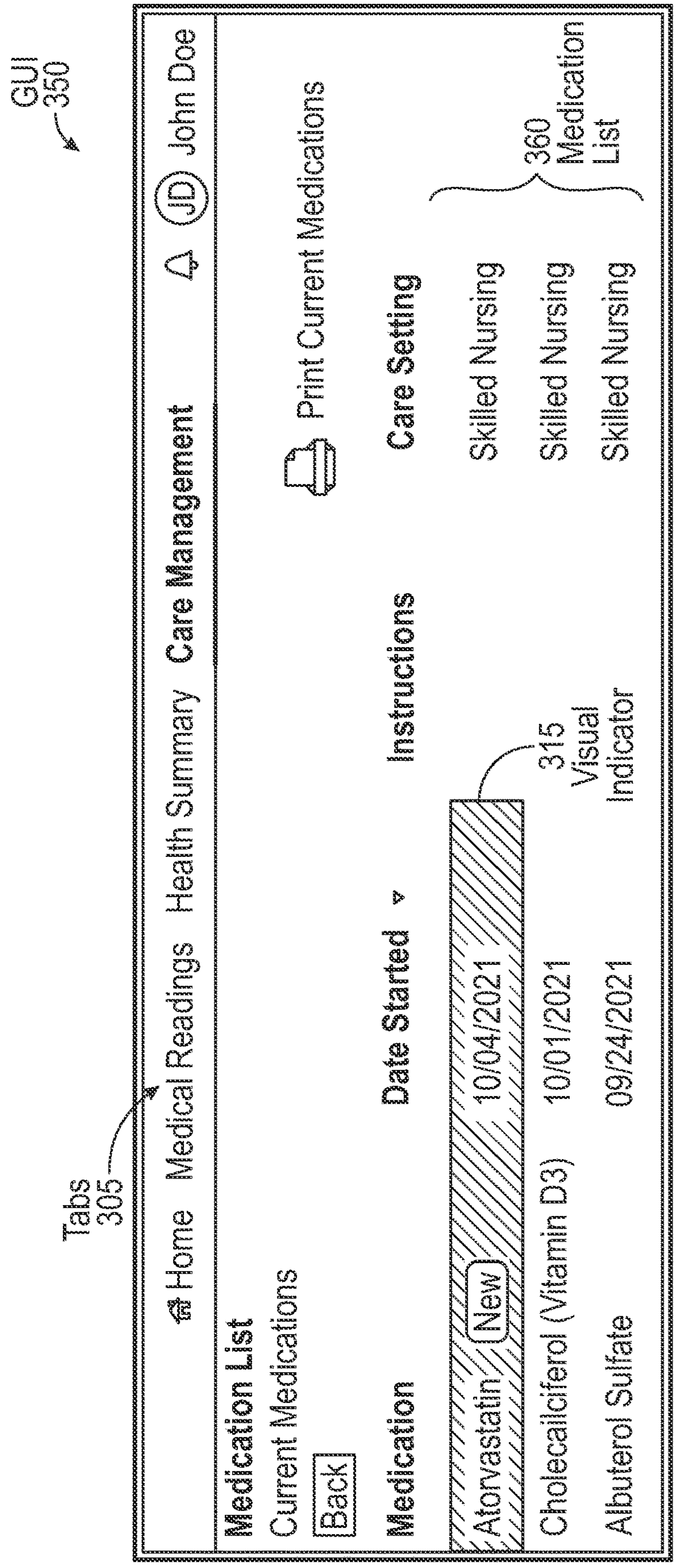

FIGS. 3A and 3B illustrate GUIs for emphasizing new information in a medical record using visual indicators, according to one embodiment. FIG. 3A illustrates a GUI 300 that includes a row of tabs 305 for navigating through the health portal. In this example, the tab "Health Summary" is selected which lists conditions and diagnostics in the person's medical record. That is, this tab displays a diagnosis list 310 which indicates the type of the diagnoses (e.g., the SNOMED Clinical Terms (CT)), a name of the diagnoses, the date of the diagnoses, the date the diagnoses ended, and any notes.

In this example, the list 310 includes three diagnoses in the medical record. It is assumed that the first diagnosis (i.e., Hyperlipidemia) is a new diagnosis that triggered an automatic notification as described in method 200. In contrast, the second and third diagnoses (i.e., Vitamin Deficiency and Encounter for surgical aftercare) are old diagnoses that were previously viewed by the authorized person. That is, it is assumed the authorized person has previously logged into the health portal to view these two diagnoses.

The GUI 300 emphasizes the first diagnosis relative to the second and third diagnoses in at least two ways. First, the first diagnosis is arranged closer to the top of the GUI 300 than the second and third diagnoses. Second, the GUI 300 includes a visual indicator 315 for the first diagnosis, but not the second and third diagnoses. The embodiments herein are not limited to any particular visual indicator 315, but include such things as bolding or italicizing the text of the first diagnosis relative to the other diagnoses, using a different font or text color for the first diagnosis relative to the other diagnoses, adding highlighting to the first diagnosis, providing a border around the first diagnosis, and the like. In this manner, the GUI 300 can visually represent the operations performed by the automated notification system such as identifying a change in the medical record, determining whether that change should be reported to an authorized person using a rule set, and transmitting a notification to the authorized person.

The GUI 300 also includes a "NEW" indicator for the first diagnosis, but not for the second and third diagnoses. In one embodiment, the "NEW" indicator and the visual indicator 315 may be displayed for the first diagnosis for a fixed time period (e.g., four days). Thus, anytime the authorized person logs into the health portal and accesses the GUI 300, it displays these indicators. Alternatively, the health portal may display the "NEW" indicator and the visual indicator 315 only the first time the authorized person logs into the portal. Once the person logs in again, the visual appearance of the first diagnosis is the same as the visual appearances of the second and third diagnosis. This is described in more detail below.

However, in another embodiment, the health portal may determine to not emphasize the second and third diagnoses even if the authorized person has not yet viewed those diagnoses. For example, these two diagnoses may be relatively minor conditions such that, according to the rule set, do not trigger an automatic notification. Thus, in this example, these conditions are added to the medical record without the system sending an electronic message to the authorized person. However, the first diagnosis, according to the rule set, does trigger an automatic notification to the authorized person. Thus, when the authorized person logs into the health portal in response to receiving the notification, even assuming she has not logged in since the second and third diagnosis were made (e.g., her last login was before 09/24/2021), the health portal does not emphasize these diagnoses in the GUI 300. Instead, only the first diagnosis is emphasized as shown in FIG. 3A. Thus, the GUI 300 visually represents the determination made by the automatic notification system of which diagnoses are important (according to the rule set) and which are not. This information is then conveyed to the authorized person.

In another embodiment, the health portal may emphasize any new diagnoses, regardless whether these diagnoses were significant enough to trigger a notification. For example, assume that the authorized person last logged in on 09/25/2021, and thus, previously viewed the third diagnosis, but did not log in until the automatic notification system transmitted a notification regarding the new, first diagnosis. That is, the second diagnosis may not have been deemed important enough to trigger a notification, while the first diagnosis was. Nonetheless, when the authorized person logs into the portal, the GUI 300 in this example would emphasize both the first and second diagnoses. For example, both of these diagnoses may have the visual indicator 315, or the first and second diagnoses may be separately grouped at the top of the GUI 300 while the third diagnosis is in a second group at the bottom of the GUI 300. In this manner, the GUI 300 visually represents the determination made by the automatic notification system of which diagnoses are new by tracking changes to the medical record and tracking when the authorized person last logged in.

FIG. 3B illustrates a GUI 350 where the "Care Management" tab of the tabs 305 has been selected which lists conditions and diagnostics in the person's medical record. That is, this tab displays a medication list 360 which indicates a name of the medication, the date the medication was started, instructions regarding the medication, and the setting in which the medication was prescribed.

In this example, the list 360 includes three medications in the medical record. It is assumed that the first medication (i.e., atorvastatin) is a new medication that triggered an automatic notification as described in method 200. In contrast, the second and third diagnoses (i.e., cholecalciferol and albuterol sulfate) are old medications that were previously viewed by the authorized person. That is, it is assumed the authorized person has previously logged into the health portal to view these two medications.

The GUI 350 emphasizes the first medication relative to the second and third medications like in GUI 300 where the first medication is arranged closer to the top of the GUI 350 than other two medications and includes the visual indicator 315. The visual indicator 315 can be any of the embodiments discussed above. The GUI 350 also includes a "NEW" indicator for the first medication, but not for the second and third medications. In one embodiment, the "NEW" indicator and the visual indicator 315 may be displayed for the first medication for a fixed time period (e.g., four days). Thus, anytime the authorized person logs into the health portal and accesses the GUI 350, it displays these indicators. Alternatively, the health portal may display the "NEW" indicator and the visual indicator 315 only the first time the authorized person logs into the portal. Once the person logs in again, the visual appearance of the first medication is the same as the visual appearances of the second and third medications.

However, in another embodiment, the health portal may determine to not emphasize the second and third medications even if the authorized person has not yet viewed those medications. For example, these two medications may be relatively minor conditions such that, according to the rule set, do not trigger an automatic notification. Thus, in this example, these conditions are added to the medical record without the system sending an electronic message to the authorized person. However, the first medication, according to the rule set, does trigger an automatic notification to the authorized person. Thus, when the authorized person logs into the health portal in response to receiving the notification, even assuming she has not logged in since the second and third medications were prescribed (e.g., her last login was before 09/24/2021), the health portal does not emphasize these medications in the GUI 350. Instead, only the first medication is emphasized as shown in FIG. 3B. Thus, the GUI 350 visually represents the determination made by the automatic notification system of which medications are important (according to the rule set) and which are not.

In another embodiment, the health portal may emphasize any new medications, regardless whether these medications were significant enough to trigger a notification. For example, assume that the authorized person last logged in on 09/25/2021, and thus, previously viewed the third medication, but did not log in until the automatic notification system transmitted a notification regarding the new, first medication. That is, the second medication may not have been deemed important enough to trigger a notification, while the first medication was. Nonetheless, when the authorized per logs into the portal, the GUI 350 in this example would emphasize both the first and second medication. For example, both of these medication may have the visual indicator 315, or the first and second medications may be separately grouped at the top of the GUI 350 while the third medication is in a second group at the bottom of the GUI 350. In this manner, the GUI 350 visually represents the determination made by the automatic notification system of which medications are new by tracking changes to the medical record and tracking when the authorized person last logged in.

The health portal and the GUIs in FIGS. 3A and 3B can be used to provide a prophylaxis treatment to the patient. For example, after being notified of a new medication, the authorized person can login and view the change as illustrated in FIG. 3B. The authorized person may be innately familiar with the patient's medical condition. Thus, the authorized person may know if the new medication may harm the patient—e.g., the GUI 350 indicates penicillin was prescribed to the patient but the authorized person knows the patient is allergic to penicillin, or a change in the patient's diet that would harm the patient. Because the authorized person was immediately notified by the system of the change, she can review the updated information using the health portal and ensure the change does not harm the patient. If it does, although not shown, the GUIs can include a selectable feedback element (e.g., an embedded link labeled "Contact the Physician") which the authorized person can use to immediately inform the physician that the change could be harmful to the patient. The physician can then receive an automated notification that includes the authorized person's comment and review the medical record. Thus, the automated notification system can be used to perform a prophylaxis treatment that includes input from the authorized person. In other embodiments, a separate GUI in the health portal can serve as a messaging interface where the authorized person can provide feedback.

While FIGS. 3A and 3B illustrate emphasizing new diagnoses and medications, the same principles can be applied when removing diagnoses and medications. For example, using FIG. 3A as an example, if the person is no longer vitamin deficient, the automatic notification system can trigger a notification to the authorized person. When she logs in, the health portal can emphasize the second diagnosis, e.g., move it to the top of the GUI 300 above the first and third diagnoses or use the visual indicator 315. For example, the visual indicator 315 may highlight the End Date field for the second diagnosis to indicate this diagnosis is no longer active (i.e., the patient has recovered from the condition).

Moreover, the same principles can be applied to other changes in a medical record besides changes to diagnoses and medications. For example, the GUIs may have a tab for dietary restrictions that lists certain foods the patient should, or should not eat, or a tab listing the current staff (physician or nurses) assigned to the patient along with their contact information. The automatic notification system could also notify the authorized person when there are changes to this information in the person's medical record.

Returning to the method 200, the block 225 includes an optional sub-block 230 where the GUI displays educational information for the update. Because the health portal may be intended for an authorized person who many not have medical training, the health portal can provide educational information regarding the update to the medical record. This is discussed in FIG. 4.

Figure 4:
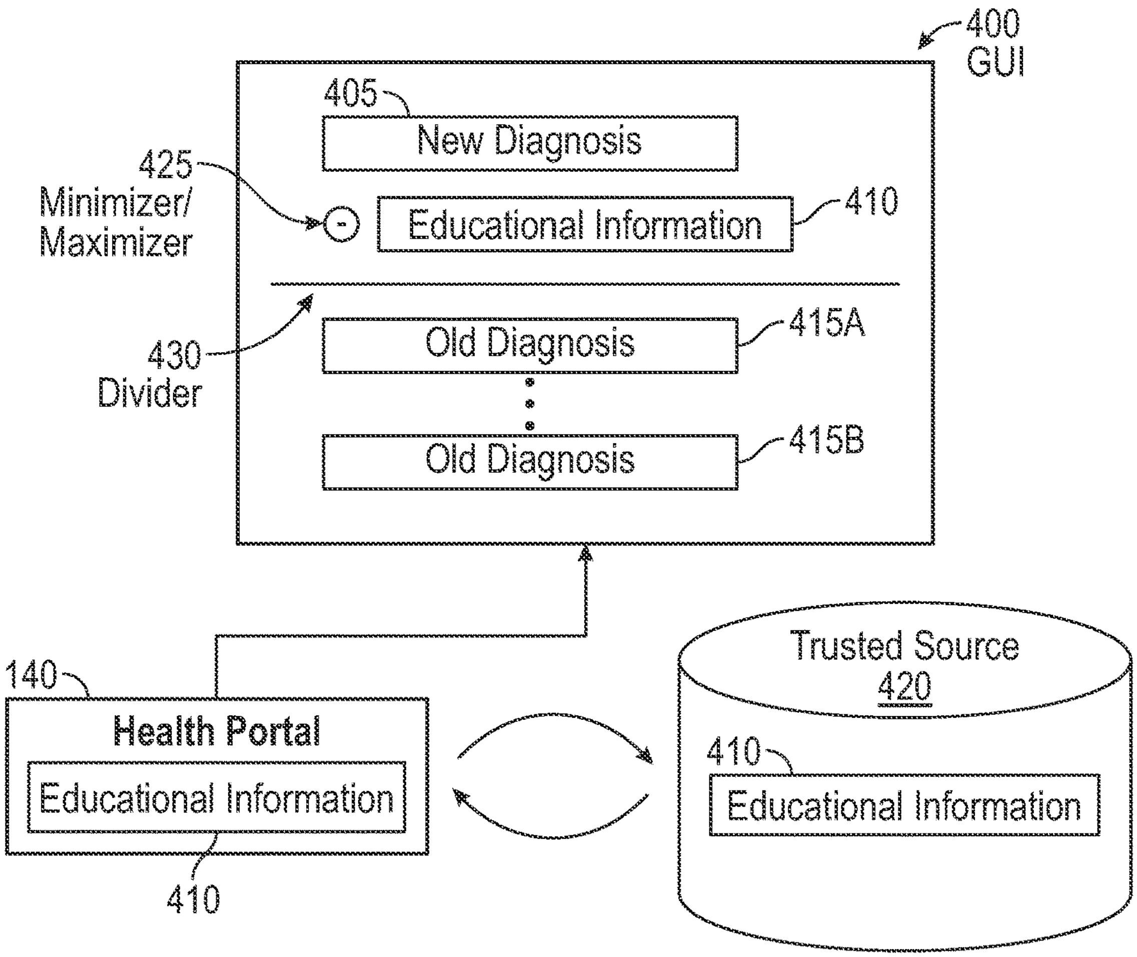
FIG. 4 illustrates a system for displaying educational information corresponding to new information in a medical history, according to one embodiment.

FIG. 4 illustrates a system for displaying educational information corresponding to new information in a medical history, according to one embodiment. FIG. 4 includes a GUI 400 which is updated to include educational information 410 by the health portal 140. In this example, a new diagnosis 405 is divided from old diagnoses 415 using a divider 430 which serves to emphasize the diagnosis 405 from the old diagnoses 415. Of course, the GUI 400 could also include visual indicators to further emphasize the new diagnosis 405.

In addition to emphasizing the new diagnosis 405, the GUI 400 displays the educational information 410 corresponding to the new diagnosis 405. For example, the educational information 410 could include a description of the diagnosis 405, its common symptoms, an expected recovery time, common treatments, and the like. In one embodiment, the educational information 410 could include a link (e.g., selectable text or URL) to other sources of information about the diagnosis 405. The link could launch a new web browser window or a different application so the authorized person can learn more about the new diagnosis 405.

The GUI 400 also includes a minimizer/maximizer 425 for minimizing or expanding the educational information 410. For example, because the amount of educational information 410 can be large, the minimizer/maximizer 425 permits the authorized person to remove or reduce the amount of space in the GUI 400 occupied by the educational information 410 so the authorized person can, e.g., view the new diagnosis 405 and the old diagnoses 415 on the same screen. The minimizer/maximizer 425 can also be used to expand the educational information 410 back to its original size after it was minimized.

FIG. 4 also illustrates the health portal 140 retrieving the educational information 410 from a trusted source 420. After identifying the new diagnosis 405, the health portal 140 can transmit the name of the diagnosis 405 (e.g., its SNOMED CT name) to the trusted source 420. The trusted source 420 can be a database (e.g., a government database or healthcare provider database) that provides educational information 410 for various medical conditions. The automated notification system may vet the trusted source 420 before pulling the educational information 410 from the source 420. That way, the health portal 140 knows it is providing reliable information to the authorized person. Providing the educational information 410 from a trusted source 420 can satisfy the authorized person's interest in the new diagnosis 405 without the person performing her own web search which can lead to less reliable sources. Thus, FIG. 4 illustrates a system where the health portal 140 can query a trusted, third-party source 420 to provide reliable educational information 410 to the authorized person via the GUI 400. Moreover, as the trusted source 420 updates its information (e.g., as more information about a condition is identified), the health portal 140 can continue to query the source 420 so it retrieves the most up-to-date educational information each time the authorized person logs in.

While FIG. 4 illustrates displaying educational information 410 for the new diagnosis 405, in another embodiment, the health portal can query the trusted source 420 to retrieve educational information for the old diagnoses 415 which is also displayed in the GUI 400. However, in one embodiment, the educational information for the old diagnoses 415 may initially be minimized in the GUI 400 when the user navigates to this portion of the health portal while the educational information for the new diagnosis 405 is initially maximized. The authorized person can then maximize the educational information for one of the old diagnoses 415 using a minimizer/maximizer 425.

Moreover, a GUI similar to the GUI 400 can also be used to provide educational information regarding other updates to a person's medical record. For example, when adding a new medication, the health portal 140 can query a trusted source to provide educational information 410 such as a description of the new medication, side effects, dosage amounts, and the like.

Figure 5:
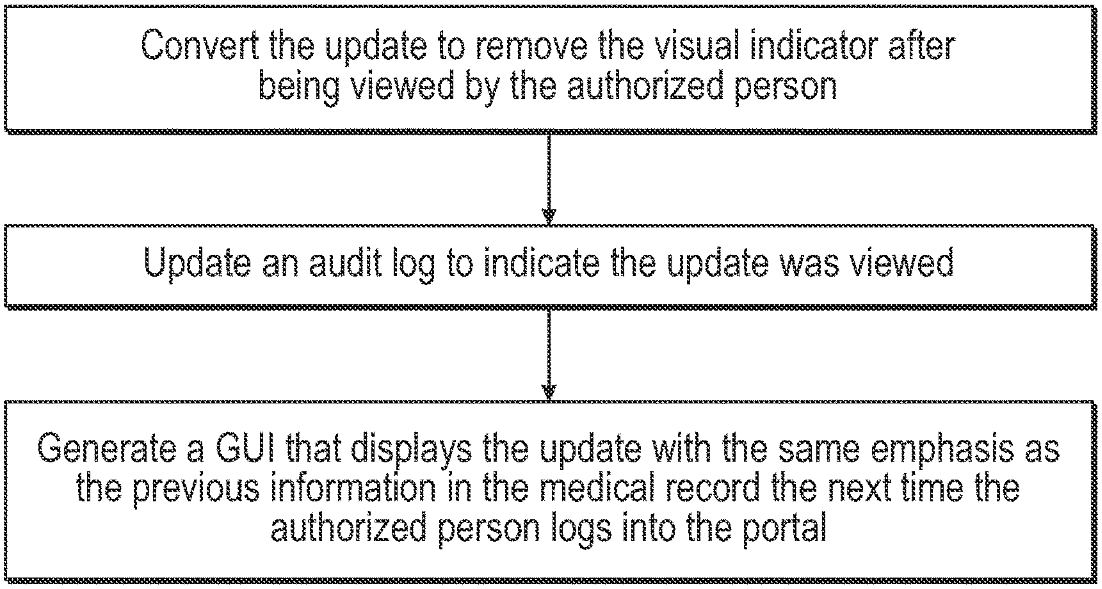
FIG. 5 is a flowchart for tracking when an authorized person has viewed new information in a medical history, according to one embodiment.

FIG. 5 is a flowchart of a method 500 for tracking when an authorized person has viewed the new information in a medical history, according to one embodiment. In one embodiment, the method 500 is performed after the method 200 where the authorized person has received an automated notification regarding an update to a person's medical record and logged into the health portal to view the updated information.

At block 505, the health portal converts the update to remove the visual indicator after being viewed by the authorized person. In one embodiment, the health portal may set a flag for the update indicating it has been viewed by the authorized person. In another embodiment, the health portal may save a timestamp corresponding to when the authorized person logged into the health portal, which can be compared to a timestamp corresponding to the update. Because the login timestamp is later in time than the update timestamp, the health portal knows the update to the medical record has been viewed by the authorized person, and thus, the visual indicator should no longer be associated with the update.

At block 510, the automated notification system updates an audit log to indicate the update was viewed. The audit log can include one or more entries indicating the changes made to the medical record as part of the update as well as a timestamp when the authorized person viewed these changes in the health portal. For example, the timestamp may indicate when the authorized person logged into the health portal, or selected a tab in a GUI listing the changes to the medical record. The audit log can then be used as a record for privacy, regulation, or legal purposes to track what persons accessed the medical record, and what changes they viewed when visiting the portal.

In addition to tracking when an authorized person logs into the portal to view the updated information, the system can add to the audit trail such events as changes to the medical record and transmitting notifications to the authorized person. That way, the audit trail can indicate when a notification was sent to the authorized person (or repeated notifications were sent to the person) and whether the authorized person then acted on those notifications by logging into the health portal. In this manner, the audit log can be used to satisfy regulatory, contractual, and legal requirements regarding the automated notification system.

At block 515, the health portal generates a GUI that displays the update with the same emphasis as the older information in the medical record the next time the authorized person logs into the portal. Because the update was converted at block 510, the next time the authorized person logs into the health portal, the information corresponding to the update is not emphasized relative to the older information in the medical record. Stated differently, the updated information is emphasized the same (e.g., without a visual indicator or being spatially separated) in the GUI as the old information in the medical record. As mentioned above, this can be tracked using flags associated with the information in the medical record, or by comparing timestamps indicating when the medical record was updated and when the authorized person last logged into the portal.

Using FIG. 3A as an example, assuming the authorized person again logs into the health portal after previously viewing the three diagnosis in the list 310, the first diagnosis would no longer have the visual indicator 315. That is, the first diagnosis may appear the same as the second and third diagnoses. This can indicate to the authorized person that she has already viewed these diagnoses—i.e., there are no new diagnoses related to the patient.

Figure 6:
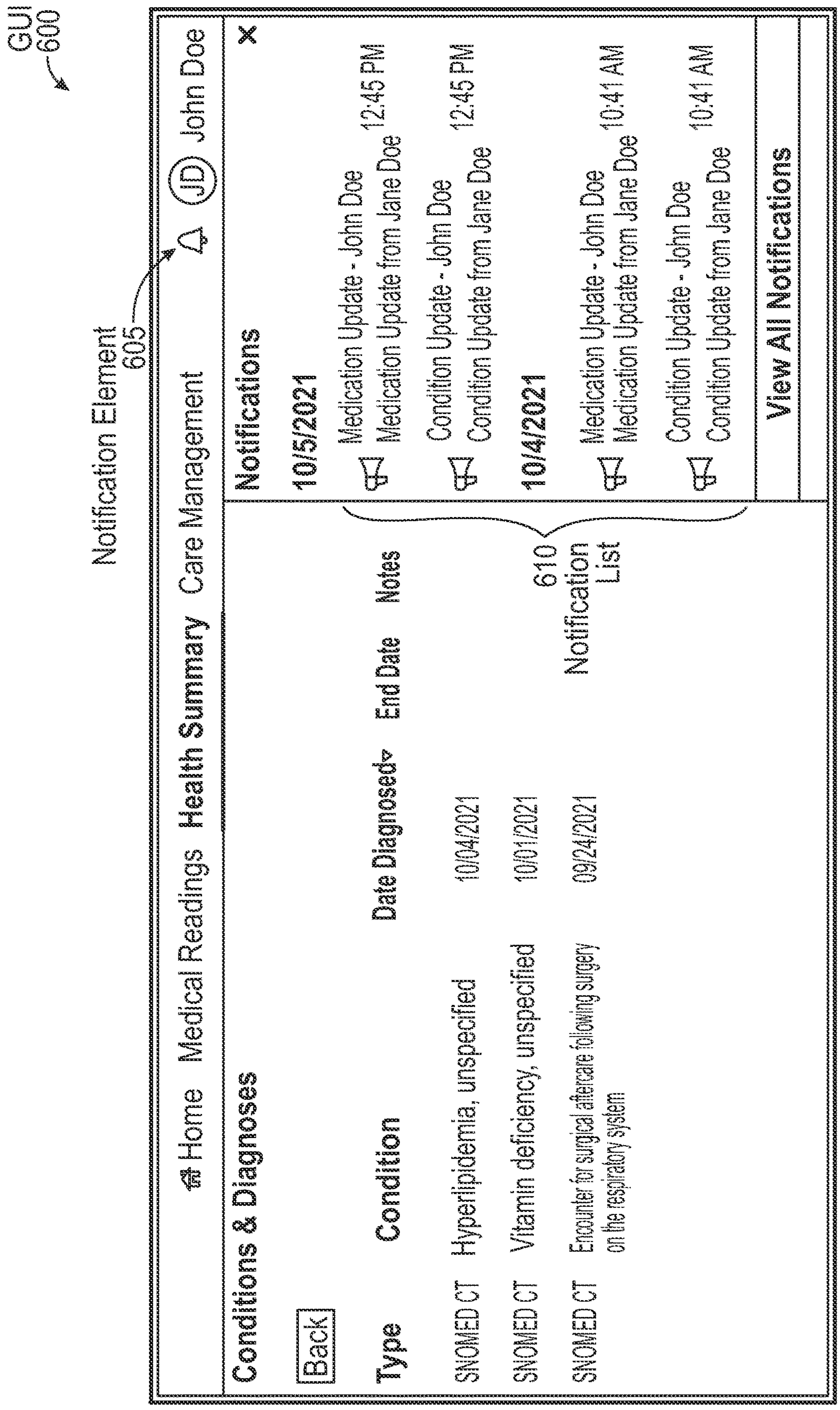
FIG. 6 is a GUI for displaying notifications corresponding to a medical history, according to one embodiment.

FIG. 6 is a GUI 600 for displaying notifications corresponding to a medical history, according to one embodiment. This GUI 600 illustrates what happens when the authorized person touches or clicks on a notification element 605 (i.e., the bell icon). Doing so opens up a notification list 610 that lists the most recent changes to the person's health record. Instead of displaying only one type of change (e.g., only new diagnoses, or only new medications), the notification list 610 can show multiple types of changes to the medical record.

In this example, the notification list 610 shows new diagnoses and new medications. Thus, the notification list 610 can show a comprehensive list of the changes to medical record (e.g., all the changes recently made to the medical record). In one embodiment, the authorized person can press or click on one of the items in the list 610 which can then change the GUI 600 to display the corresponding tab so the person can view more information. For example, if the user clicks on the first Medication Update in the list 610, the health portal updates the GUI 600 to display the Care Management tab which can provide more information about that medication update (e.g., the information illustrated in FIG. 3B).

Moreover, the GUI 600 can illustrate that the visual emphasis has been removed because the user has previously viewed the new information. That is, unlike in FIG. 3A where the first condition has a visual indicator 315, in GUI 600 the visual indicator has been removed, thereby indicating to the authorized person that they have already view this condition.

Like the GUI 300, the GUI 600 includes a row of tabs for navigating through the health portal. In this example, the tab "Health Summary" is selected which lists conditions and diagnostics in the person's medical record. That is, this tab displays the diagnosis list that indicates the type of the diagnoses (e.g., the SNOMED Clinical Terms (CT)), a name of the diagnoses, the date of the diagnoses, the date the diagnoses ended, and any notes. In this example, the diagnoses list includes the same three diagnoses as in the GUI 300. However, it is assumed that the first diagnosis (i.e., Hyperlipidemia) is no longer a new diagnosis. As such, the first diagnosis has similar visual characteristics with the second and third diagnoses (i.e., Vitamin Deficiency and Encounter for surgical aftercare) since all three are considered old diagnoses that were previously viewed by the authorized person. That is, it is assumed the authorized person has previously logged into the health portal to view these three diagnoses.

In this manner, the GUI 600 can visually represent previously viewed diagnoses in the same manner. These diagnoses can have the same visual characteristics even if they were viewed by the authorized person at different times. For example, the person may have first logged in to view the bottom diagnosis in the list, then logged in to view the middle diagnosis, and then later logged in to view the top diagnosis. Nonetheless, the GUI 600 does not visually emphasis one of the diagnosis more than the other.

However, in another embodiment, the GUI 600 could apply different visual characteristics to the previously viewed diagnoses. For example, as the diagnoses age, the system may fade them out using light shades of text. For instance, a previously viewed diagnosis that is more than a month old may be displayed using the lightest shade of text, while a previously viewed diagnosis that is less than a month old but more than a week old has a darker shade of text, and a previously viewed diagnosis that is less than a week old has the darkest shade of text. In any case, the visual indicators or visual emphasis assigned to the previously viewed diagnoses may be different than the visual indicators assigned to new, previously unseen diagnoses. That way, the authorized person can still quickly distinguish between previously viewed diagnoses (which may have different shades of text) from new diagnoses (which may have highlighting or bright outlines).

Figure 7:
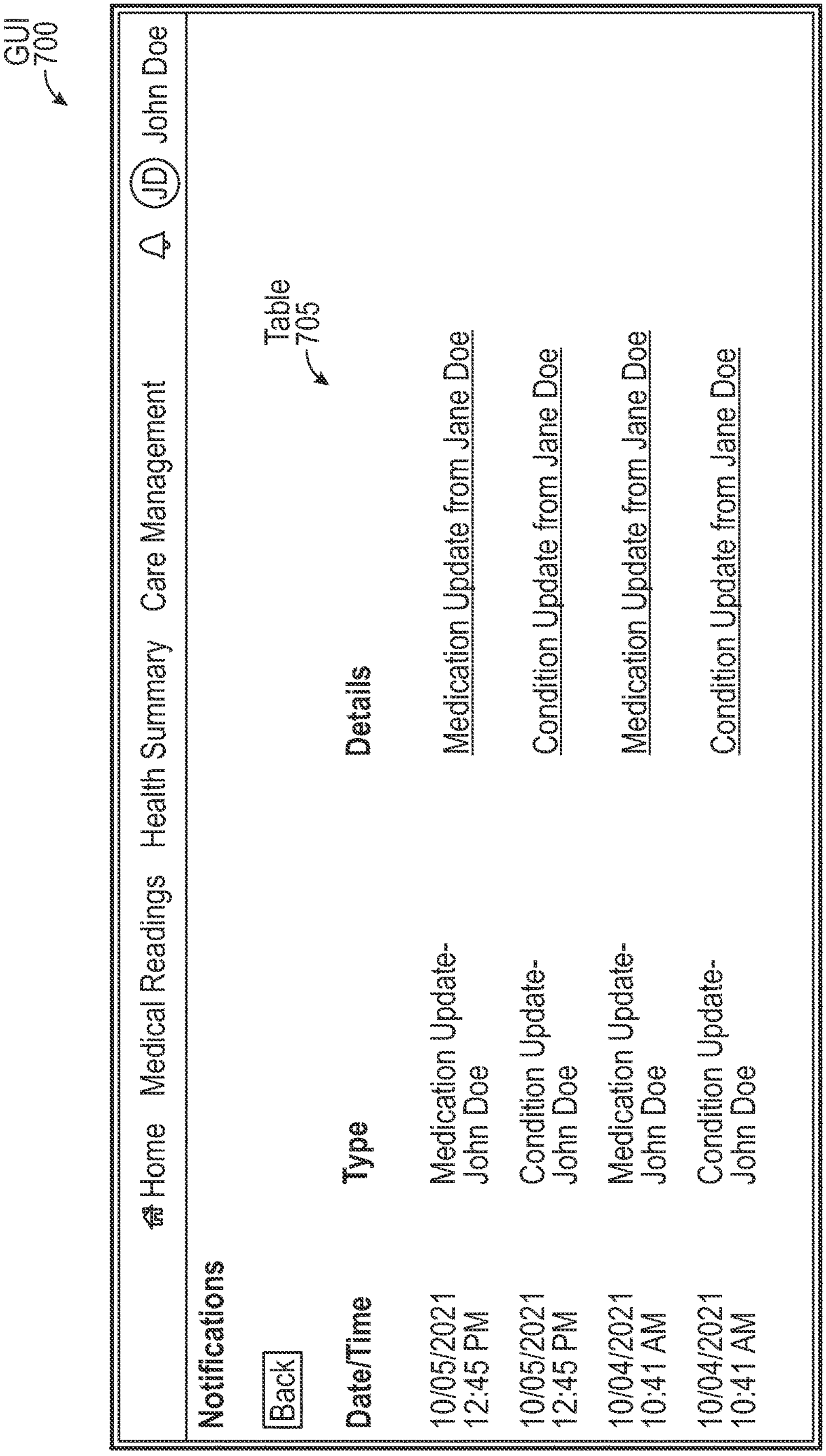
FIG. 7 is a GUI for displaying notifications corresponding to a medical history, according to one embodiment.

FIG. 7 is a GUI 700 for displaying notifications corresponding to a medical history, according to one embodiment. In this GUI 700, the notifications are displayed in a table 705. In one example, the table 705 is displayed in the GUI 700 when the user selects the "View All Notifications" in the GUI 600 in FIG. 6. Like the notification list 610 in GUI 600, the table 705 can display changes made to multiple types of information in the medical record (e.g., both diagnoses and medications). Thus, the notification list 610 in GUI 600 and the table 705 in GUI 700 can provide comprehensive lists of the changes made to the medical record. However, because of differences in the formats, the notification list 610 may display only a limited number of updates (e.g., the four most recent updates to the medical record). If the authorized person wants to see previous updates, she can select the "View All Notifications" link in GUI 600 which causes the health portal to display the GUI 700 that includes the table 705 that lists all the updates to the medical record.

In this example, the table 705 includes four medication updates in the medical record. In some embodiment, the first medication update in the table 705 may be a new prescription that triggered an automatic notification as described in method 200. In contrast, the second, third, and fourth updates may be old diagnoses that were previously viewed by the authorized person. That is, it is assumed the authorized person has previously logged into the health portal to view these three updates.

In one embodiment, the GUI 700 can emphasize the first medication update relative to the second, third, and fourth medication updates in at least two ways. First, the first updated can be arranged closer to the top of the GUI 700 than the second, third, and fourth updates. Second, the GUI 700 can include a visual indicator like the visual indicator 315 in GUI 300 for the first medication update, but not the second, third, and fourth updates. The embodiments herein are not limited to any particular visual indicator, but include such things as bolding or italicizing the text of the first medication updates relative to the other medication updates, using a different font or text color for the first update relative to the other updates, adding highlighting to the first update, providing a border around the first update, and the like. In this manner, like GUIs 300 and 350, the GUI 700 can visually represent the operations performed by the automated notification system such as identifying a change in the medical record, determining whether that change should be reported to an authorized person using a rule set, and transmitting a notification to the authorized person.

However, in another embodiment, the health portal may determine to not emphasize the second, third, and fourth updates even if the authorized person has not yet viewed those updates. For example, these three updates may correspond to over-the-counter drugs such that, according to the rule set, do not trigger an automatic notification. Thus, in this example, these updates are added to the medical record without the system sending an electronic message to the authorized person. However, the first medication update, according to the rule set, does trigger an automatic notification to the authorized person. Thus, when the authorized person logs into the health portal in response to receiving the notification and navigates to the table 705, even assuming she has not logged in since the second, third, and fourth updates were made (e.g., her last login was before 10/04/2021), the health portal does not emphasize these updates in the GUI 700. Instead, only the first medication update is emphasized. Thus, like the GUIs 300 and 350, the GUI 700 can visually represents the determination made by the automatic notification system of which medication updates are important (according to the rule set) and which are not. This information is then conveyed to the authorized person.

In another embodiment, the health portal may emphasize any new medication updates, regardless whether these diagnoses were significant enough to trigger a notification. For example, assume that the authorized person last logged in on 10/4/2021 after 10:41 AM, and thus, previously viewed the third and fourth updates, but did not log in until the automatic notification system transmitted a notification regarding the new, first and second updates. When the authorized person logs into the portal, the GUI 700 in this example emphasizes both the first and second medication updates. For example, both of these updates may have a visual indicator in the table 705, or the first and second updates may be separately grouped at the top of the table 705 while the third and fourth updates are in a second group at the bottom of the table 705. In this manner, the GUI 700 visually represents the determination made by the automatic notification system of which medication updates are new by tracking changes to the medical record and tracking when the authorized person last logged in.

EXAMPLE COMPUTING HARDWARE

Figure 8:
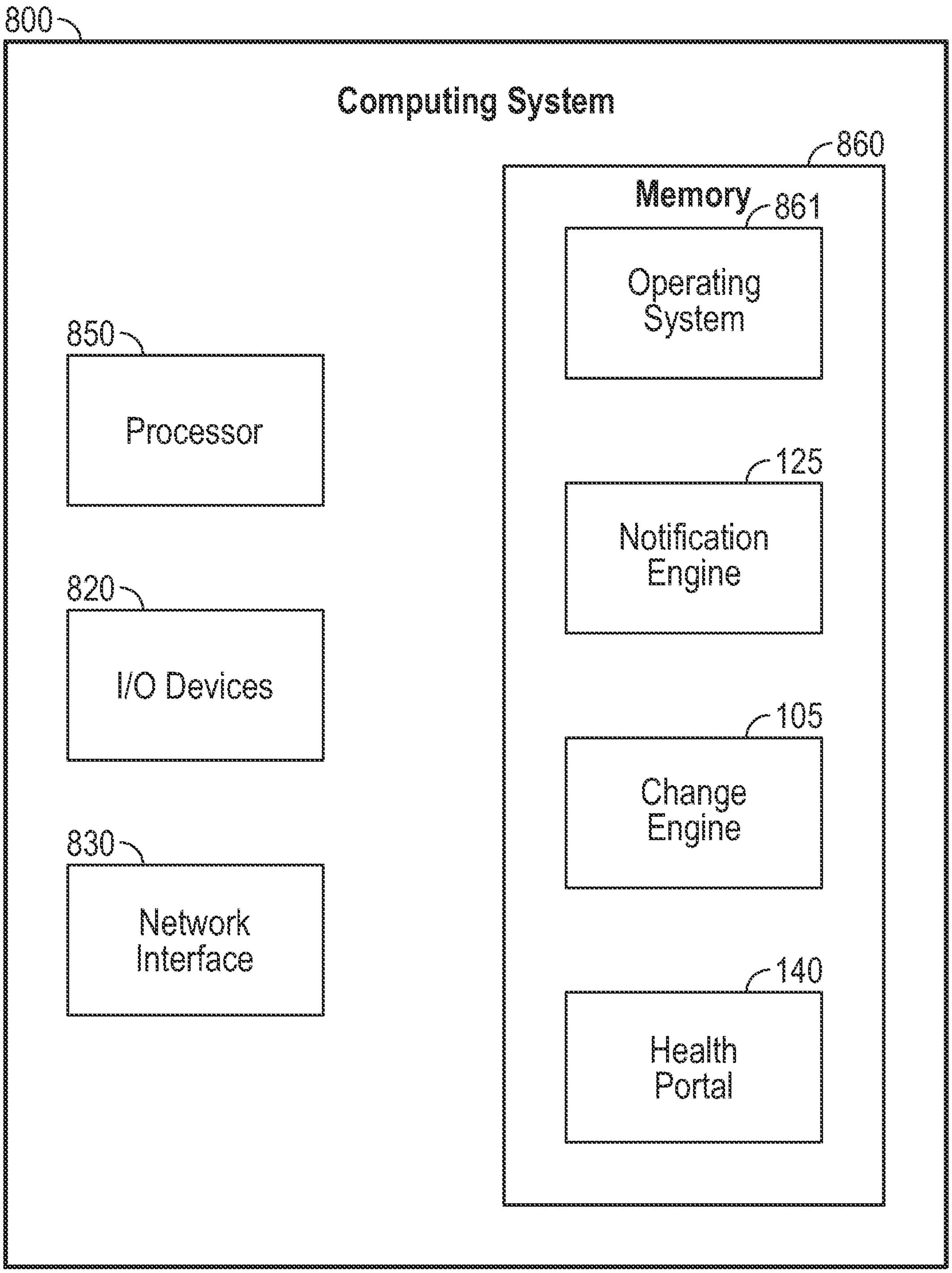
FIG. 8 is a computing system, according to one embodiment.

FIG. 8 illustrates a computing system 800, which may be used to implement the automated notification system 100 in FIG. 1 (e.g., a computer, a laptop, a tablet, a smartphone, web server, data center, cloud computing environment, etc.), or any other computing device described in the present disclosure. As shown, the computing system 800 includes, without limitation, a processor 850 (e.g., a central processing unit), a network interface 830, and memory 860. The computing system 800 may also include an input/output (I/O) device interface connecting I/O devices 820 (e.g., keyboard, display and mouse devices) to the computing system 800.

The processor 850 retrieves and executes programming instructions stored in the memory 860 (e.g., a computer readable medium). Similarly, the processor 850 stores and retrieves application data residing in the memory 860. An interconnect facilitates transmission, such as of programming instructions and application data, between the processor 850, I/O device interface, storage, network interface 830, and memory 860. The memory 860 is generally included to be representative of volatile and non-volatile memory elements. For example, the memory 860 can include random access memory and a disk drive storage device. Although shown as a single unit, the memory 860 may be a combination of fixed and/or removable storage devices, such as magnetic disk drives, flash drives, removable memory cards or optical storage, network attached storage (NAS), or a storage area-network (SAN). The memory 860 may include both local storage devices and remote storage devices accessible via the network interface 830. As shown, the notification engine 125, change engine 105, and health portal 140 are maintained in the memory 860 to provide perform the functions described above.

As shown, the memory 860 includes an operating system 861. The operating system 861 may facilitate receiving input from and providing output to various components. For example, the network interface 830 can be used to output the GUIs to display the tags along with their visual indicators. Further, the network interface can be used to provide GUIs to the authorized person and receive input from the person.

Further, the computing system 800 is included to be representative of a physical computing system as well as virtual machine instances hosted on a set of underlying physical computing systems. Further still, although shown as a single computing device, one of ordinary skill in the art will recognize that the components of the computing system 800 shown in FIG. 8 may be distributed across multiple computing systems connected by a data communications network.

The processor 850 can be any electronic circuitry, including, but not limited to one or a combination of microprocessors, microcontrollers, application specific integrated circuits (ASIC), application specific instruction set processor (ASIP), and/or state machines, that communicatively couples to memory and controls the operation of the change engine 105, the notification engine 125, and the health portal 140 which can be software applications executed by the processors. The processor 850 may be 8-bit, 16-bit, 32-bit, 64-bit or of any other suitable architecture. The processor 850 may include an arithmetic logic unit (ALU) for performing arithmetic and logic operations, processor registers that supply operands to the ALU and store the results of ALU operations, and a control unit that fetches instructions from memory and executes them by directing the coordinated operations of the ALU, registers and other components. The processor 850 may include other hardware that operates software to control and process information. The processor 850 executes software stored on the memory 860 to perform any of the functions described herein. The processor 850 controls the operation and administration of the change engine 105, the notification engine 125, and the health portal 140 in the automated notification system 100, as well as the notification service 165, by processing information. The processor 850 is not limited to a single processing device and may encompass multiple processing devices.

As discussed, the memory 860 may include any one or a combination of volatile or non-volatile local or remote devices suitable for storing information. For example, the memory may include random access memory (RAM), read only memory (ROM), magnetic storage devices, optical storage devices, or any other suitable information storage device or a combination of these devices. The software represents any suitable set of instructions, logic, or code embodied in a computer-readable storage medium. For example, the software may be embodied in the memory, a disk, a CD, or a flash drive. In particular embodiments, the software may include an application executable by the processors to perform one or more of the functions described herein.

ADDITIONAL CONSIDERATIONS

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word "exemplary" means "serving as an example, instance, or illustration." Any aspect described herein as "exemplary" is not necessarily to be construed as preferred or advantageous over other aspects.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A method, comprising:

receiving an initial update to a medical record of a patient from a healthcare professional;

determining, using a rule set, that one or more authorized users should be notified of the initial update;

generating a notification for the one or more authorized users corresponding to the initial update;

initiating a transmission of an electronic communication to the one or more authorized users over a network in real time that comprises the notification;

authenticating the one or more authorized users at a health portal;

after authenticating the one or more authorized users, generating a graphical user interface (GUI) comprising a visual indicator to emphasize the initial update to the medical record relative to older information in the medical record also displayed in the GUI, wherein the GUI is accessible by the one or more authorized users in real time, and generating the visual indicator comprises:

determining, based on a timestamp of a previous interaction by a respective authorized user with the health portal, one or more portions of the medical record that were previously viewed;

identifying the initial update as new information relative to the previously viewed portions; and converting the GUI from a first display format to a second display format, comprising rearranging content within the GUI to display the initial update in a position above the previously viewed portions of the medical record and applying the visual indicator to the initial update, wherein, in the second display format, the initial update is displayed in a top section of the GUI with a visual highlight, and the previously viewed portions of the medical record are displayed in a bottom section, below the top section, of the GUI;

upon determining, based on interaction data associated with the one or more authorized users, that the initial update has been viewed by the one or more authorized users, converting the GUI from the second display format back to the first display format, comprising removing the visual indicator from the initial update and restoring the initial update from the position above the previously viewed portions of the medical record to a defined position within the GUI; and in response to receiving an additional update to the medical record, converting the GUI from the first display format back to the second display format, comprising:

rearranging the additional update to a position above previously viewed portions, including the initial update, of the medical record; and applying the visual indicator to the additional update.

2. The method of claim 1, further comprising:

receiving a second update to the medical record;

determining, using the rule set, that none of the one or more authorized users should be notified of the second update, wherein the rule set indicates which types of changes to the medical record do, and do not, trigger an automatic notification to the one or more authorized users; and updating the medical record without transmitting an electronic communication to any of the one or more authorized users.

3. The method of claim 2, wherein the rule set indicates that some types of new diagnoses or new medications trigger the automatic notification while other types of new diagnoses or new medications do not trigger the automatic notification.

4. The method of claim 1, further comprising:

generating a selectable link to the health portal, wherein the selectable link is included in the electronic communication to the respective authorized user and, when selected by the respective authorized user, launches an application to access the health portal.

5. The method of claim 1, wherein the visual highlight comprises at least one of (i) altering a font style, color, or layout of text displayed in the GUI for the initial update to the medical record relative to text displayed in the GUI for the older information in the medical record, (ii) adding a highlight color to the text displayed in the GUI for the initial update to the medical record, (iii) adding a border around the text displayed in the GUI for the initial update to the medical record, or (iv) displaying a "NEW" indicator associated with the text displayed in the GUI for the initial update to the medical record.

6. The method of claim 1, wherein generating the GUI comprises:

retrieving educational information corresponding to the initial update from a trusted, third-party source; and embedding the educational information in the GUI proximate to text describing the initial update.

7. The method of claim 6, wherein the educational information comprises at least one of: (i) text describing a new diagnosis or new medication in the initial update or (ii) a selectable link to the third-party source that describes the new diagnosis or new medication in the initial update.

8. The method of claim 1, further comprising:

after receiving a feedback via a selectable feedback element, transmitting the feedback to a healthcare professional who initiated the initial update.

9. The method of claim 1, further comprising:

updating, in response to initiating the transmission of the electronic communication, an audit log to indicate the notification was transmitted to the one or more authorized users; and updating, in response to generating the GUI, the audit log to indicate the initial update was viewed by the respective authorized user.

10. A non-transitory computer readable medium comprising instructions to be executed in a processor, the instructions when executed in the processor perform an operation, the operation comprising:

receiving an initial update to a medical record of a patient from a healthcare professional;

determining, using a rule set, that one or more authorized users should be notified of the initial update;

generating a notification for the one or more authorized users corresponding to the initial update;

initiating a transmission of an electronic communication to the one or more authorized users over a network in real time that comprises the notification;

authenticating the one or more authorized users at a health portal;

after authenticating the one or more authorized users, generating a graphical user interface (GUI) comprising a visual indicator to emphasize the initial update to the medical record relative to older information in the medical record also displayed in the GUI, wherein the GUI is accessible by the one or more authorized users in real time, and generating the visual indicator comprises:

determining, based on a timestamp of a previous interaction by a respective authorized user with the health portal, one or more portions of the medical record that were previously viewed;

identifying the initial update as new information relative to the previously viewed portions; and converting the GUI from a first display format to a second display format, comprising rearranging content within the GUI to display the initial update in a position above the previously viewed portions of the medical record and applying the visual indicator to the initial update, wherein, in the second display format, the initial update is displayed in a top section of the GUI with a visual highlight, and the previously viewed portions of the medical record are displayed in a bottom section, below the top section, of the GUI;

upon determining, based on interaction data associated with the one or more authorized users, that the initial update has been viewed by the one or more authorized users, converting the GUI from the second display format back to the first display format, comprising removing the visual indicator from the initial update and restoring the initial update from the position above the previously viewed portions of the medical record to a defined position within the GUI; and in response to receiving an additional update to the medical record, converting the GUI from the first display format back to the second display format, comprising:

rearranging the additional update to a position above previously viewed portions, including the initial update, of the medical record; and applying the visual indicator to the additional update.

11. The non-transitory computer readable medium of claim 10, wherein the operation further comprises:

receiving a second update to the medical record;

determining, using the rule set, that none of the one or more authorized users should be notified of the second update, wherein the rule set indicates which types of changes to the medical record do, and do not, trigger an automatic notification to the one or more authorized users; and updating the medical record without transmitting an electronic communication to any of the one or more authorized users.

12. The non-transitory computer readable medium of claim 10, wherein the operation further comprises:

generating a selectable link to the health portal, wherein the selectable link is included in the electronic communication to the respective authorized user and, when selected by the respective authorized user, launches an application to access the health portal.

13. The non-transitory computer readable medium of claim 10, wherein the visual highlight comprises at least one of (i) altering a font style, color, or layout of text displayed in the GUI for the initial update to the medical record relative to text displayed in the GUI for the older information in the medical record, (ii) adding a highlight color to the text displayed in the GUI for the initial update to the medical record, (iii) adding a border around the text displayed in the GUI for the initial update to the medical record, or (iv) displaying a "NEW" indicator associated with the text displayed in the GUI for the initial update to the medical record.

14. The non-transitory computer readable medium of claim 10, wherein generating the GUI comprises:

retrieving educational information corresponding to the initial update from a trusted, third-party source; and embedding the educational information in the GUI proximate to text describing the initial update, wherein the educational information comprises at least one of: (i) text describing a new diagnosis or new medication in the initial update or (ii) a selectable link to the third-party source that describes the new diagnosis or new medication in the initial update.

15. The non-transitory computer readable medium of claim 10, wherein the operation further comprises:

after receiving a feedback via a selectable feedback element, transmitting the feedback to a healthcare professional who initiated the initial update.

16. The non-transitory computer readable medium of claim 10, wherein the operation further comprises:

updating, in response to initiating the transmission of the electronic communication, an audit log to indicate the notification was transmitted to the one or more authorized users; and updating, in response to generating the GUI, the audit log to indicate the initial update was viewed by the respective authorized user.

17. A system, comprising:

a processor; and a memory comprising instructions that, when executed by the processor, perform an operation, the operation comprising:

receiving an initial update to a medical record of a patient from a healthcare professional;

determining, using a rule set, that one or more authorized users should be notified of the initial update;

generating a notification for the one or more authorized users corresponding to the initial update;

initiating a transmission of an electronic communication to the one or more authorized users over a network in real time that comprises the notification;

authenticating the one or more authorized users at a health portal;

after authenticating the one or more authorized users, generating a graphical user interface (GUI) comprising a visual indicator to emphasize the initial update to the medical record relative to older information in the medical record also displayed in the GUI, wherein the GUI is accessible by the one or more authorized users in real time, and generating the visual indicator comprises:

determining, based on a timestamp of a previous interaction by a respective authorized user with the health portal, one or more portions of the medical record that were previously viewed;

identifying the initial update as new information relative to the previously viewed portions; and converting the GUI from a first display format to a second display format, comprising rearranging content within the GUI to display the initial update in a position above the previously viewed portions of the medical record and applying the visual indicator to the initial update, wherein, in the second display format, the initial update is displayed in a top section of the GUI with a visual highlight, and the previously viewed portions of the medical record are displayed in a bottom section, below the top section, of the GUI;

upon determining, based on interaction data associated with the one or more authorized users, that the initial update has been viewed by the one or more authorized users, converting the GUI from the second display format back to the first display format, comprising removing the visual indicator from the initial update and restoring the initial update from the position above the previously viewed portions of the medical record to a defined position within the GUI; and in response to receiving an additional update to the medical record, converting the GUI from the first display format back to the second display format, comprising:

rearranging the additional update to a position above previously viewed portions, including the initial update, of the medical record; and applying the visual indicator to the additional update.

18. The system of claim 17, wherein the operation further comprises:

receiving a second update to the medical record;

determining, using the rule set, that none of the one or more authorized users should be notified of the second update, wherein the rule set indicates which types of changes to the medical record do, and do not, trigger an automatic notification to the one or more authorized users; and updating the medical record without transmitting an electronic communication to any of the one or more authorized users.

19. The system of claim 17, wherein the operation further comprises:

updating, in response to initiating the transmission of the electronic communication, an audit log to indicate the notification was transmitted to the one or more authorized users; and updating, in response to generating the GUI, the audit log to indicate the initial update was viewed by the respective authorized user.

* * * * *